United States Patent [19]

Tritsarolis

[11] Patent Number: 5,242,952
[45] Date of Patent: Sep. 7, 1993

[54] FACIAL SKIN MOISTURIZING COMPOSITION

[76] Inventor: Dimitrios Tritsarolis, 4616 E. 49 St., Cuyahoga Heights, Ohio 44125

[21] Appl. No.: 899,256

[22] Filed: Jun. 16, 1992

[51] Int. Cl.⁵ .......................... A61K 7/48; A61K 9/06; A61K 9/10
[52] U.S. Cl. ................................. 514/783; 424/195.1; 514/844; 514/847; 514/969
[58] Field of Search ............... 514/844, 847, 969, 783; 424/195.1

[56] References Cited

PUBLICATIONS

Bennett, 1937, The Cosmetic Formalary pp. 3, and 43.
Pharmaceutical Formulas, 1944, pp. 175 and 174.
The Extra Pharmacopolia, 1941, vol. I, 22nd edition, pp. 100, 101; 102, 129–132, 745, 761; 762 and 1230; Martindale.

*Primary Examiner*—Dale R. Ore
*Attorney, Agent, or Firm*—J. Helen Slough

[57] ABSTRACT

A skin moisturizing composition of lard leaf, natural mint, and virgin olive oil is produced by heating the lard leaf preferably to a temperature around 240° F., adding the natural mint and heating preferably to about 360° F., cooling the heated mixture and adding the virgin olive oil at a mixture temperature preferably about 120° F.

6 Claims, No Drawings

FACIAL SKIN MOISTURIZING COMPOSITION

This invention pertains to a facial moisturizing cream and more particularly to a facial moisturizing cream adapted to smooth facial lines and wrinkles, reduce inflamation and diminish dark rings below the eyes in addition to moisturizing facial skin.

BACKGROUND OF THE INVENTION

A constant need exists for improved cosmetic facial creams adapted to treat aging skin conditions where facial skin undergoes an aging process and tends to form lines, wrinkles, dry skin, dark rings, and attendant inflamations of the skin. The pharmaceutical and cosmetic industry has long suggested the use of natural oils and the avoidance of artificial ingredients for the treatment of skin problems. For instance, U.S. Pat. No. 4,936,986 discloses a moisturizing lotion based on a blend of peanut oil, rose water, olive oil, anhydrous lanolin, and natural lemon oil while specifically avoiding artificial ingredients, preservatives, emulsifiers, or alcohol. The lotion is said to moisturize and restore oil to the treated skin areas. Similarly, U.S. Pat. No. 5,002,974 discloses a moisturizing composition for treating dry skin based on an oil phase in an aqueous phase where surface active agents assist in forming a stable oil-in-water emulsion. Useful oils suggested include animal oils, fish oils, vegetable oils, mineral oils, and synthetic oils. U.S. Pat. No. 4,569,839 discloses a hair and skin cosmetic utilizing pulverized powder derived from natural plants such as trees and shrubs or from roots, stems, leaves, flowers, fruits or seeds. The natural plant powder is dispersed into a fluid cohesion agent containing an organic solvent, fatty oils, thickening agents, emulsifying agents, and an emulsion component. Useful fatty oils include mineral oils, animal oils, vegetable oils, synthetic oils, triglycerides of synthetic fatty acids, fatty alcohols, and esters of fatty acids. Early patents such as U.S. Pat. Nos. 144,405 and 122,621 suggest the use of lard in the preparation of salves for treatment of skin cuts, burns, and scratches.

It now has been found that a facial treatment composition comprising a facial moisturizing cream based on a particular step-wise process for combining fresh lard leaf, natural mint and virgin olive oil together in a homogeneous fluid cream provides an excellent treatment for facial skin. The moisturizing cream of this invention consists of natural ingredients only and is particularly effective for moisturizing dry skin, restoring natural oils to the skin, smooth aging lines and wrinkles, reduces puffiness and dark circles below the eyes, and similar disorders of the skin. These and other advantages of the invention will become more apparent by referring to the detailed description and illustrative example of the invention.

SUMMARY OF THE INVENTION

Briefly, the invention pertains to a moisturizing cream comprising by weight between about 0.7% and 1.1% natural mint, between about 1.6% and 2.4% virgin olive oil, with the balance being leaf lard, where the leaf lard is first heated above about 220° F., then the mint is added to the preheated leaf lard while further heating to above 330° F. with mixing to form a uniform heated mixture, cooling the mixture to at least about 130° F., and then adding the virgin olive oil with mixing to provide a uniform mixture. The resulting composition is cooled to room temperature and is particularly useful as a moisturizing cream in accordance with this invention.

DETAILED DESCRIPTION OF THE INVENTION

The moisturizing cream of this invention comprises leaf lard, natural mint, and virgin olive oil processed together in a step-wise process to produce a uniform mixture of components.

Referring first to lard leaf, lard is a soft white solid or semisolid fat comprising primarily fatty acid triglycerides derived from rendering fatty tissue of a hog. Leaf fat is that fat which lines the abdominal cavity and encloses the hog kidneys. Leaf lard is a high quality lard made from leaf fat. Leaf lard is the desired lard used in the composition of this invention.

The second component used in the moisturizing cream of this invention comprises natural mint. Mint is a natural occurring aromatic plant known as Mentha. The preferred mint for use in this invention is dried natural mint. On a weight basis, the moisturizing cream comprises at least 0.7% and preferably between about 0.9% and 1.1% dried natural mint.

The third component of the moisturizing cream of this invention comprises virgin olive oil. Olive oil is the natural fixed oil expressed from ripe olives grown on cultivated olive trees and primarily containing mixed glycerides of oleic acid. Virgin olive oil can be recovered from the olive fruit in hydraulic presses where the oil is separated from the pulp without further processing. The oil recovered is virgin olive oil in an unrefined state which is the olive oil particularly useful in this invention. On a weight basis, the moisturizing cream of this invention comprises at least about 1.6% and preferably between about 2% and 2.4% virgin olive oil.

Preferred moisture cream compositions consist of on a weight basis between 0.7% and 1.1% dry natural mint, between 1.6% and 2.4% virgin olive oil, with the balance being leaf lard.

In accordance with the process of this invention, fresh lard leaf is heated sufficiently while mixing to form a fluid liquid and preferably to a temperature above about 220° F. but below a temperature, preferably less than about 260° F. to avoid burning or scorching of the heated leaf lard. Stirring or mixing is required to avoid hot spots and scorching. In the second step, the dried natural mint is added at 240° F. more or less with mixing to at least about 330° F. and preferably to about 360° F. more or less. After reaching 360° F. more or less, the heat source is removed and, while still hot, the mixture is preferably strained through a porous fabric such as double fine cheesecloth. Thereafter, the strained mixture is cooled to below about 130° F. and preferably to about 120° F. more or less. In the third step, the virgin olive oil is added to the mixture at a temperature of about 120° F. more or less and then cooled to room temperature. The resulting composition is a suitable moisture cream consisting of the natural ingredients of lard leaf, dried natural mint, and olive oil, where the moisture cream is particularly suitable for use as a facial cream for treating dry skin, reducing puffiness and dark rings, and similar skin disorders as well as smoothing lines and wrinkles.

The merits of this invention are further illustrated by the following example.

EXAMPLE

The following ingredients were mixed together in the indicated ratio and processed in the manner indicated to produce a moisturizing cream.

| a) | Ingredients | Weight % |
|---|---|---|
| | 8 ounces (volume) fresh leaf lard medium chopped | 97.1 |
| | 2 grams dried natural mint | 0.9 |
| | 1 tablespoon virgin olive oil | 2.0 | b) Processing Procedure

The leaf lard was placed in a stainless steel container and heated moderately with stirring for about 7 minutes until the melted leaf lard reached a temperature of about 240° F. Stirring was sufficient to avoid burning or scorching of the liquid leaf lard. The heat was increased in conjunction with adding of the dried natural mint along with stirring for about 5 minutes until the mixture reached a temperature of about 360° F. The heated mixture was removed from the heat source and strained through double-fine cheesecloth. The strained mixture was then cooled until the mixture temperature reached about 120° F. whereupon the virgin olive oil was added. The resulting mixture was stirred to form a uniform mixture and cooled to room temperature for use as a moisture cream. The moisture cream was found to be particularly effective for moisturizing dry skin, reducing puffiness in the skin, smoothing lines and wrinkles, and diminishing dark circles below the eyes.

Although the moisture cream of this invention is described particularly in respect to specific preferred embodiments of the invention, the invention is not intended to be limited except by the appended claims.

What I claim is:

1. A skin moisturizing composition consisting essentially of:
   at least 0.7% by weight natural mint;
   at least 1.6% by weight virgin olive oil;
   with the balance being lard; and
   where the moisturizing cream is produced by first heating the leaf lard to a temperature above about 220° F. to form liquid leaf lard, adding the dried natural mint to the heated leaf lard to form a liquid mixture in conjunction with upheating the liquid mixture to above about 333° F. to form a heated mixture of leaf lard and mint, removing the heat and straining the heated mixture of leaf lard and mint, cooling the heated mixture to below about 130° F. then adding the virgin olive oil and stirring to form a uniform moisturizing cream.

2. The composition of claim 1 where the skin moisturizing composition consists of between 0.7% and 1.1% by weight dried natural mint, between 1.6% and 2.4% by weight virgin olive oil, with the balance being leaf lard.

3. The composition of claim 1 where the skin moisturizing composition consists of about 0.9% by weight dried natural mint, about 2% virgin olive oil, with the balance being leaf lard.

4. A process for producing a skin moisturizing composition, consisting of on a weight basis, between 0.7% and 1.1% natural mint, between about 1.6% and 2.4% virgin olive oil, with the balance being lard, the process step comprising:
   heating the leaf lard to a temperature above about 220° F. to form heated liquid leaf lard;
   adding the natural mint to the heated liquid leaf lard to form a mixture while heating the mixture to a temperature above about 330° F.;
   removing the heat and straining the mixture;
   cooling the strained mixture to below about 130° F.; and
   adding the virgin olive oil and mixing to form a uniform composition of moisturizing skin cream.

5. The process of claim 3 where the leaf lard is heated to about 240° F., followed by heating the mixture of lard leaf and natural mint to about 360° F., and adding the virgin olive oil to the strained mixture at temperature above 120° F.

6. The process of claim 4 where the virgin olive oil is added to the strained mixture temperature of about 120° F.

* * * * *